United States Patent [19]

Ishikawa

[11] Patent Number: 4,582,572

[45] Date of Patent: Apr. 15, 1986

[54] METHOD FOR DETECTING END POINT OF TITRATION

[75] Inventor: Seiji Ishikawa, Sagamihara, Japan

[73] Assignee: Mitsubishi Kasei Kogyo Kabushiki Kaisha, Tokyo, Japan

[21] Appl. No.: 608,965

[22] Filed: May 10, 1984

[30] Foreign Application Priority Data

May 16, 1983 [JP] Japan .................................. 58-85565

[51] Int. Cl.[4] ........................................... G01N 27/42
[52] U.S. Cl. ...................................... 204/1 T; 422/77
[58] Field of Search ...................... 204/1 M, 1 T, 405; 422/76, 77

[56] References Cited

U.S. PATENT DOCUMENTS

| | | | |
|---|---|---|---|
| 3,248,309 | 4/1966 | Robinson | 204/1 T |
| 3,398,064 | 8/1968 | Propst | 204/1 T |
| 3,563,875 | 2/1971 | Coulson | 204/405 |
| 3,593,119 | 7/1971 | Brum et al. | 204/1 T |
| 3,647,668 | 3/1972 | Lindblad et al. | 204/1 T |
| 3,879,604 | 4/1975 | Malmvig | 422/76 X |
| 3,950,237 | 4/1976 | Arawa et al. | 204/405 |

OTHER PUBLICATIONS

G. Svehla, "Automatic Potentiometric Titration", 1st Ed., Oxford, New York, 1978.

*Primary Examiner*—Andrew H. Metz
*Assistant Examiner*—Nam X. Nguyen
*Attorney, Agent, or Firm*—Oblon, Fisher, Spivak, McClelland & Maier

[57] ABSTRACT

An end point of polarization titration is detected by the steps of passing constant DC pulse having a magnitude of 0.1–100 $\mu A$ between a pair of detection electrodes immersed in a solution to be titrated, detecting a polarization state generated between the detection electrodes at each current passage before the polarization reaches an equilibrium state and judging the end point based on the detected polarization state. The polarization state is detected by integrating a polarization potential generated at each current passage and the polarization is eliminated by short circuiting the detection electrodes before passing the next DC pulse.

14 Claims, 4 Drawing Figures

METHOD FOR DETECTING END POINT OF TITRATION

BACKGROUND OF THE INVENTION

This invention relates to a method and apparatus for detecting or judging an end point of polarization titration during analysis of a solution.

When analyzing a solution by polarization titration it is essential to accurately detect the end point of titration. In this specification, a term "titration" is used to include both a method of so-called volume titration in which a titration reagent is introduced into a solution to be titrated and a so-called coulometric titration method in which a titration reagent is formed in a solution to be titrated by electrolysis. Although many methods of judging the end point of titration have been known, according to one method, a pair of platinum detection electrodes are immersed in a solution to be titrated, and a small current is passed between the detection electrodes from a source of constant current so as to judge the end point from the magnitude of polarization potential generated across the electrodes. This method utilizes a phenomenon that the polarization potential varies greatly near the end point of titration, and is used widely as a method of detecting the end point at the time of measuring water content according to Karl Fisher titration process. Among other methods of detecting the end point of titration are included iodometric titration and other oxidation-reduction titrations, and a method of measuring iodine and bromine numbers of fats and oils.

Direct current or alternating current is used for generating polarization between the detection electrodes, but with DC, although the variation in the polarization potential near the end point is large, the polarization potential tends to vary due to the influence of stirring of the solution which makes it difficult to accurately judge the end point. Although the method of using alternating current is not affected by stirring, it accompanies a problem that the variation in the polarization potential near the end point is small which also makes it difficult to accurately detect the end point. These problems can be eliminated to some extent as disclosed in Japanese Pat. No. 933,388.

SUMMARY OF THE INVENTION

It is an object of this invention to provide a novel method and apparatus capable of accurately detecting or determining the end point of polarization titration without the problems in the prior art methods described above.

Another object of this invention is to provide a method and apparatus capable of accurately detecting the end point of polarization titration in accordance with the polarization state of the detection electrodes.

Still another object of this invention is to provide a method and apparatus wherein the end point of titration can be accurately detected by measuring water content according to Karl Fisher titration process.

Briefly stated, according to this invention these and other objects can be accomplished by passing constant pulse shaped direct current through a solution to be titrated.

According to one aspect of this invention, there is provided a method of judging an end point of polarization titration comprising the steps of intermittently passing constant direct current between a pair of detection electrodes immersed in a solution to be titrated, detecting a polarization state generated between the detection electrodes at each current passage before the polarization reaches an equilibrium state, and judging the end point of titration based on the detected polarization state.

According to another aspect of this invention there is provided apparatus for detecting an end point of polarization titration comprising a pair of detection electrodes immersed in a solution to be titrated, means for periodically passing constant direct current between the detection electrodes, means for short circuiting the detection electrodes, and means for integrating polarization potential of the detection electrodes generated during current passage therebetween, the short circuiting means operating in an interval between completion of the operation of the integrating means and commencement of next current passage so as to eliminate polarization between the detection electrodes.

According to a modification of this invention, there is provided apparatus for detecting an end point of polarization titration comprising a pair of detection electrodes immersed in a solution to be titrated, means for periodically passing constant direct current between the detection electrodes, means for short circuiting the detection electrodes and means for detecting polarization potential between the detection electrodes, the short circuit means operating in each period during an interval between completion of the operation of the detecting means and commencement of next current passage so as to eliminate polarization between the detection electrodes.

DESCRIPTION OF THE PREFERRED EMBODIMENTS

As above described, according to this invention, a pair of detection electrodes are immersed in a solution to be titrated and a small constant direct current is intermittently passed through the detection electrodes. Hereinafter, this intermittent direct current is called a pulse shaped direct current. The magnitude of the current is selected to be in a range not affecting the titration, usually in a range of 0.1–100 $\mu A$, more preferably 1–50 $\mu A$. Passage of current generates a polarization potential across the detection electrodes and as the current flow is continued, the magnitude of the polarization potential increases with time and then reaches a definite value, that is equilibrium state determined by the concentration of a substance to be titrated contained in the solution. However, as the polarization proceeds further, the polarization potential tends to vary due to the influence of stirring of the solution, so that this influence becomes remarkable near the end point of titration. According to this invention, the end point of titration is judged based on the build up portion of the polarization potential of a time-polarization potential curve during an interval in which polarization is progressing which starts immediately following the current passage.

Figure 1:
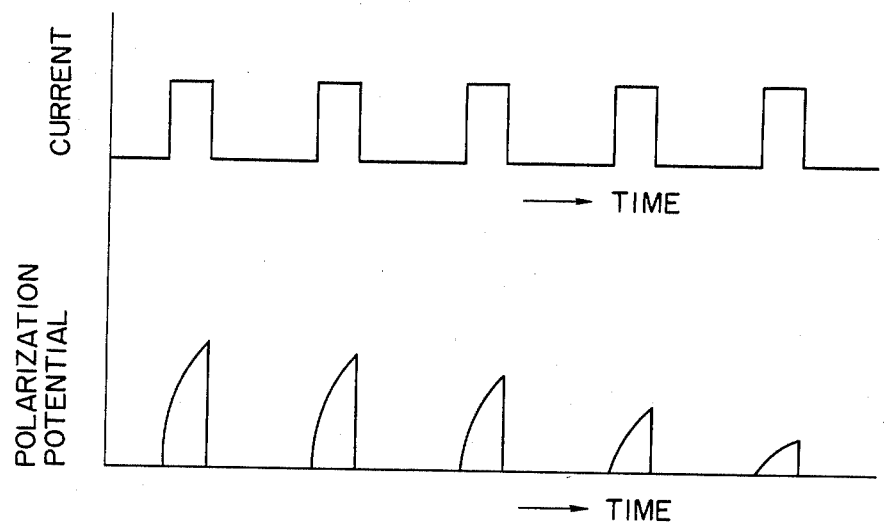
FIG. 1 is a diagrammatic representation showing the relation between pulse shaped constant direct current and a polarization generated thereby.

FIG. 1 shows the relation between pulse shaped direct current and variation with time in the magnitude of the polarization potential where water content is measured according to Karl Fisher titration process. In FIG. 1, the upper curve shows the pulse shaped constant DC titration current, whereas the lower curve shows the manner of decreasing with time of the polarization potential. As can be noted from FIG. 1, where the pulse shaped constant direct current is passed according to this invention, the polarization occurs immediately after passage of the current. At this time, since the polarization potential is not caused to vary due to stirring of the solution, where the build up portion of the polarization potential of the time-polarization curve is utilized, it is possible to accurately judge the end point of titration since sufficiently high and stable polarization potential can be utilized.

Judgement of the end point of the titration based on the polarization potential according to this invention can be made by either a method wherein the judgement is made based on the polarization potential itself or a method in which the judgement is made based on a time integral of the polarization potential.

According to the former method, after commencing the passage of the pulse shaped current, the polarization potential is measured at a point where the effect of stirring the solution does not yet appear even though the polarization has proceeded substantially, and when the measured potential coincides with a preset end point potential this point is judged as the end point of titration. Usually, the polarization potential is measured at a point about 10–200 ms, preferably 20–100 ms, later than the commencement of current flows. When the measurement is made earlier than this point, the polarization has not yet proceeded sufficiently, so that the polarization potential is small, thus degrading the measurement accuracy. Conversely, when the measurement is made later than this point, the polarization potential tends to vary due to the effect of stirring the solution.

According to the latter method, the polarization potential is integrated for an interval between commencement of current passage and a point at which polarization has considerably proceeded but the effect of stirring the solution does not yet reach a substantial value, and a point at which the integrated value coincides with a preset value is judged as the end point of titration. The integration may be started at any point subsequent to the commencement of current flow so that it is advantageous to start the integration concurrently with the current passage. Usually, the integration is made for at least 10 ms, preferably at least 20 ms starting from the time of commencement of current passage. However, the integration may be started after a predetermined time has elapsed subsequent to the commencement of current flow. This latter method gives larger and more stable measured value than the former method in which the end point is determined in accordance with the polarization potential itself. However, if the integration time is too short the measurement accuracy decreases also. For the purpose of obviating the adverse effect of stirring the solution, it is usual to terminate the integration at a point later by 200 ms, preferably 100 ms than the commencement of current passage. For this reason, it is advantageous to perform integration for at least 10 ms during a period of 200 ms subsequent to the commencement of current flow, preferably for at least 20 ms during a period of 100 ms subsequent to the commencement of current flow. It is more advantageous to start integration concurrently with the commencement of current flow and to terminate the integration in a period of 20–100 ms after starting current flow.

With either one of the two methods, the current is interrupted at a time when the measurement or integration of the polarization potential has completed, and polarization is ceased for preparing for the next current flow. In other words, in our invention it is preferable to substantially eliminate polarization at a time when a pulse shaped direct current is started to flow between detection electrodes. If current flow is started in the presence of polarization between the detection electrodes, correct time-polarization curve would not be manifested. To eliminate the polarization between the detection electrodes, they may be electrically short circuited, which is effective to rapidly eliminate the polarization.

Figure 2:
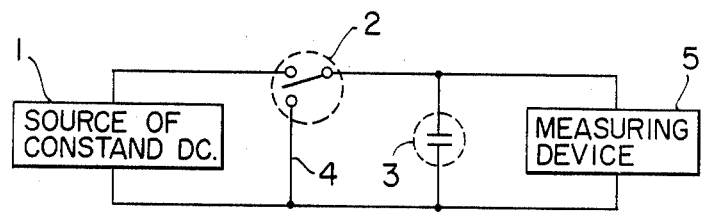
FIGS. 2 and 3 show examples of polarization potential detection apparatus embodying the invention.

In FIG. 2 showing one example of the apparatus for detecting the end point of titration according to this invention, constant direct current is passed between a pair of detection electrodes 3 from a source of constant direct current 1 through a transfer switch 2. When the switch 2 is transferred to the lower terminal to interrupt the connection between the source 1 and the detection electrodes 3, these electrodes are short circuited through a conductor 4 to eliminate polarization. Connected in parallel with the detection electrodes 3 is a measuring device 5 which measures the polarization potential at a point later than the commencement of current flow, by a definite interval, or measures with time the polarization potential and then integrates the measured polarization potential for a predetermined interval.

Figure 3:
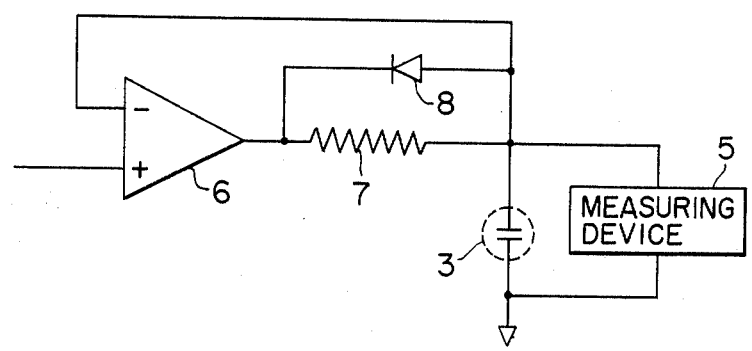

While in FIG. 2, the detection electrodes 3 are short circuited by a transfer switch 2, in a modification shown in FIG. 3, the detection electrodes are short circuited through a differential amplifier 6. Thus, when a pulse voltage is applied to the positive input terminal of the differential amplifier 6, constant direct current outputted from the amplifier is supplied to the detection electrodes 3 via a high resistance 7 to create a polarization potential between the detection electrodes. When application of the pulse voltage to the amplifier is interrupted, current flows in the opposite direction through a diode 8 into the amplifier until the polarization between the detection electrodes disappears.

Figure 4:
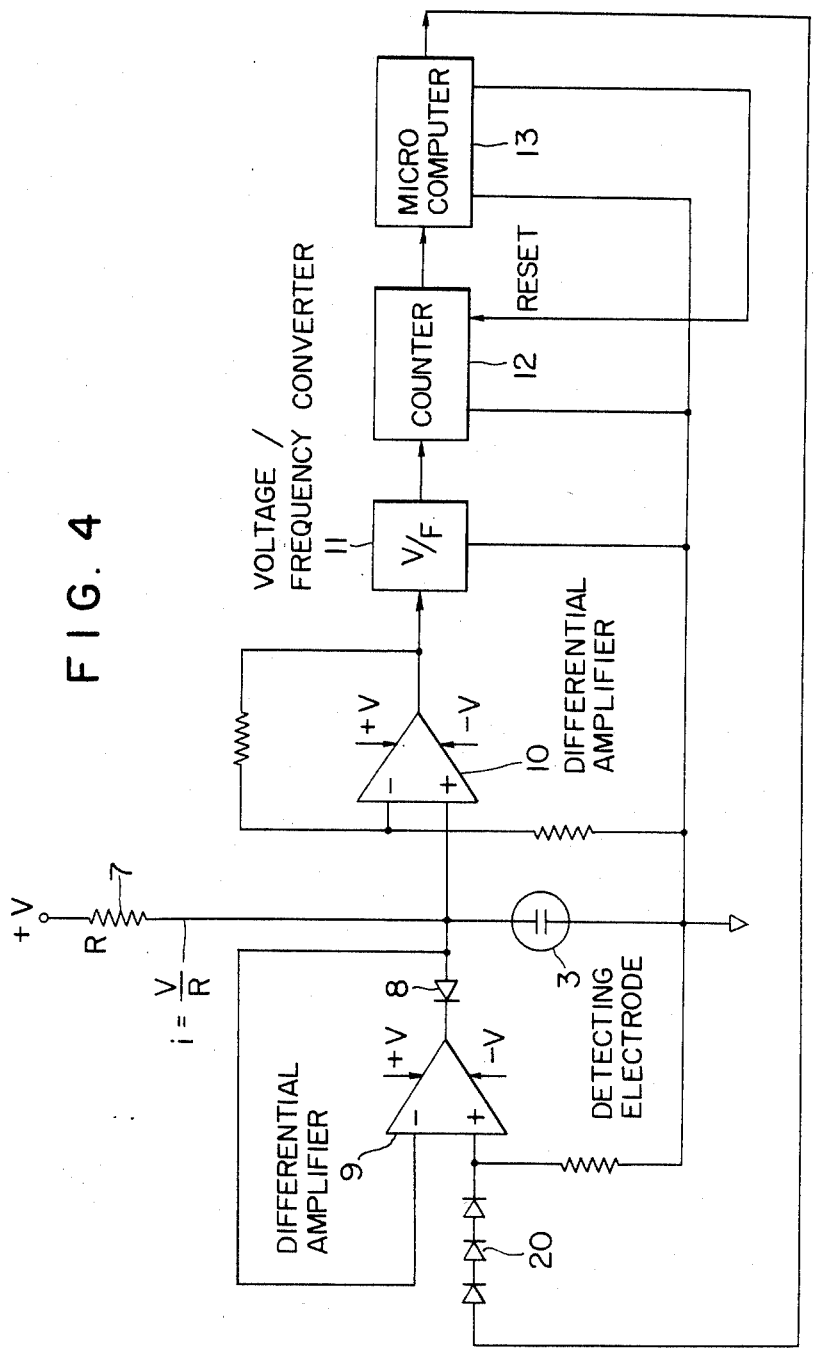
FIG. 4 is a connection diagram showing another example of polarization potential detection apparatus utilizing a microcomputer.

Although in the circuit shown in FIG. 3, the source of constant current and short circuiting circuit are combined by the amplifier 6, the source of constant current and the short circuiting circuit can be separated as shown in FIG. 4. In FIG. 4 the constant direct current is supplied at a constant voltage through a high resistance 7, while the short circuiting circuit is constituted by three serially connected diodes 20, a differential amplifier 9, and a diode 8 connected to the output terminal of differential amplifier 9 while a pulse voltage produced by a microcomputer 13 is being applied to the positive input terminal of the differential amplifier 9. Then the constant direct current flows between the detection electrodes, whereby formation of the polarization proceeds. When generation of the pulse voltage from the microcomputer is interrupted, the voltage impressed upon the positive input terminal of differential amplifier 9 would be completely cut off even when a small positive voltage remains. As a consequence, current flows to the differential amplifier 9 from the detection electrodes 3 via diode 8 thus eliminating the polarization between the detection electrodes 3.

The polarization voltage of the detection electrodes is amplified by a differential amplifier 10 and then converted into a frequency by voltage/frequency (V/F) convertor 11, the number of pulses being counted by a counter 12. Concurrently with the interruption of the generation of the pulse voltage from the microcomputer 13, the counting operation of the counter 12 terminates, and the count of the counter 12 is inputted to the microcomputer to be compared with a predetermined end point voltage. Immediately prior to the generation of the next pulse voltage, the microcomputer 13 supplies a reset signal to the counter 12 so as to reset the same. The circuit shown in FIG. 4 is constructed such that the polarization potential is integrated while the pulse voltage is being applied to differential amplifier 9, that is while the constant direct current is flowing through the detection electrodes whereby the polarization is proceeding. However, if desired, the integration may be made in response to an instruction from the microcomputer 13 only during a limited interval while the polarization is proceeding.

Even when the apparatus is left as it is after interruption of the pulse current flowing through the detection electrodes, the polarization would gradually disappear. In an ordinary titration operation, however, since an interval between interruption of the pulse current and an instant at which the next pulse current starts to flow is short, the polarization cannot be sufficiently eliminated without short circuiting the detection electrodes, which degrades the accuracy of judgement of the titration end point.

According to this invention, however, the next pulse current can be passed immediately after elimination of the polarization. Consequently, if desired several tens measurements can be made per second, but about 10 measurements per second is ordinarily sufficient.

In the method of detecting coulometric titration of this invention, it is preferable to send electric current to the electrolytic electrodes not at the same time as that to the detection electrodes when controlling electrolytic current, more particularly, controlling electrolytic quantity of electrolysis (electrolytic current) based on the difference between the result of detection of polarization state of coulometric titration solution and polarization state of predetermined end titration point.

If the supply of electric current to the electrolytic electrodes and to the detection electrodes is made at the same time as is done in the prior process of generating polarization state with alternating current or direct current, it is necessary to isolate the supply of electric current to the electrolytic electrodes from the supply of electric current to the detection electrodes so that the former may not affect the latter.

To have better understanding of this invention, the following example is given.

A test was made by utilizing a coulometric titrating apparatus having an electrolytic cell in which an anode chamber and a cathode chamber are separated by a porous diaphragm. About 100 ml of commercially available coulometric anode solution AQUAMICRON A was charged in the anode chamber, and AQUAMICRON C was charged in the cathode chamber. (AQUAMICRON is a registered trade mark of Mitsubishi Kasei Kogyo Kabushiki Kaisha). A pair of platinum wires were used as the detection electrodes and a circuit similar to that shown in FIG. 4 was used as the detection apparatus of the titration end point. About 25 $\mu$A direct current having a period of about 0.4 sec. was passed through the detection electrodes for 40 ms, and control of the titrating electric quantity and detection of the end point were made by using the integrated value of the polarization voltage for 40 ms. The titration was made by passing constant direct current between generating electrodes during an interval in which no current was passed between the detection electrodes, and the electric quantity was determined by the integrated value of the polarization voltage immediately preceding the current flow. After incorporating into the anode solution 50 $\mu$l of water containing methanol containing 4 mg of water/ml with an injector, and above described titration was repeated five times to obtain the following results.

| Test Number | Measured Value ($\mu$g) |
| --- | --- |
| 1 | 198.2 |
| 2 | 198.5 |
| 3 | 198.5 |
| 4 | 198.2 |
| 5 | 198.0 | wherein the mean value $\overline{X}$ was 198.3 $\mu$g, standard deviation S was 0.22 $\mu$g and coefficient of variation was 0.11%.

Similar tests were repeated five times except that 100 $\mu$l of water containing methanol containing 20 mg of water/ml was injected into the anode solution to obtain the following results.

| Test Number | Measured Value ($\mu$g) |
| --- | --- |
| 1 | 1991.1 |
| 2 | 1991.4 |
| 3 | 1991.1 |
| 4 | 1991.9 |
| 5 | 1992.3 | wherein
$\overline{X} = 1991.6$ $\mu$g
$S = 0.53$ $\mu$g and
$CV = 0.027\%$.

These test results show that the accuracy of detection of this invention is very high.

I claim:

1. A method of determining the end point of a polarization titration, comprising the steps of:
   intermittently passing constant direct current between a pair of detection electrodes immersed in a solution to be titrated;
   detecting the polarization state generated between said detection electrodes at each current passage before said polarization reaches an equilibrium state; and
   determine the end point of the titration based on said detected polarization state.

2. The method according to claim 1 wherein said polarization state between said detection electrodes is eliminated after detecting said polarization state at each current passage and then said direct current is passed again between said detection electrodes.

3. The method according to claim 2 wherein said polarization is eliminated by short circuiting said detection electrodes.

4. The method according to claim 1 wherein said polarization state is detected by integrating for a predetermined interval a polarization potential generated at each current passage.

5. The method according to claim 4 wherein said integration of said polarization potential is made for at least 10 ms during a period of 200 ms subsequent to commencement of each current passage.

6. The method according to claim 4 wherein said integration of said polarization potential is made for at least 20 ms during a period of 100 ms subsequent to commencement of each current passage.

7. The method according to claim 4 wherein said integration of said polarization potential is started concurrently with commencement of each current passage, and terminated at a time of 20-100 ms later than the commencement of said current passage.

8. The method according to claim 1 wherein said polarization state is detected by measuring a polarization potential at a time for a predetermined interval after commencement of each current passage.

9. The method according to claim 8 wherein a polarization potential is measured at a time in a range of 10-200 ms subsequent to commencement of each current passage.

10. The method according to claim 8 wherein said polarization potential is measured at a time in a range of 20-100 ms subsequent to commencement of each current passage.

11. The method according to claim 1 wherein said titration is effected by titrating the water content of a sample with the Karl Fisher volume titration process.

12. The method according to claim 1 wherein said titration is effected by titrating the water content of a sample with the Karl Fisher coulometric titration process.

13. The method according to claim 1 wherein said constant direct current is a pulse having a magnitude of 0.1-100 $\mu$A.

14. A method of determining the end point of a polarization titration, comprising the steps of:
passing for a definite time a constant direct current of 0.1-100 $\mu$A through a pair of detection electrodes immersed in a solution to be titrated;
integrating the polarization potential generated between said detection electrodes for a time of at least 10 ms during a period of about 200 ms subsequent to commencement of current passage between said detection electrodes;
eliminating the state of polarization between said detection electrodes after completion of said integration;
repeating the above described steps of detecting the polarization state; and
determining the end point when said integrated value reaches a preset value.

* * * * *